United States Patent [19]

Richardson

[11] Patent Number: 4,498,193
[45] Date of Patent: Feb. 5, 1985

[54] JAMMER TRANSMITTER

[75] Inventor: Christopher K. Richardson, Romsey, England

[73] Assignee: Plessey Overseas Limited, Ilford, England

[21] Appl. No.: 509,397

[22] Filed: Jun. 30, 1983

[30] Foreign Application Priority Data

Jul. 1, 1982 [GB] United Kingdom ............... 8219063
Nov. 22, 1982 [GB] United Kingdom ............... 8233226

[51] Int. Cl.³ ............................................. H04K 3/00
[52] U.S. Cl. ...................................................... 455/1
[58] Field of Search ..................... 455/1, 101, 103; 343/18 E; 375/1

[56] References Cited

U.S. PATENT DOCUMENTS

| | | | |
|---|---|---|---|
| 3,774,208 | 11/1973 | Dorn et al. | 455/1 |
| 3,942,179 | 3/1979 | Dorn | 455/1 |
| 4,039,954 | 8/1977 | Den Toonder | 455/1 |
| 4,103,236 | 7/1978 | Deserno | 455/1 |
| 4,214,208 | 7/1980 | O'Donell | 455/1 |

Primary Examiner—Jin F. Ng
Attorney, Agent, or Firm—Fleit, Jacobson, Cohn & Price

[57] ABSTRACT

A jammer transmitter having a comb spectrum generator which includes a pulse generator adapted to produce a pulse train at a frequency corresponding to the channel spacing of signals to be jammed, and a bandpass filter which has a passband including a bandwidth occupied by the signals to be jammed and which is responsive to the pulse train for providing within this bandwidth comb generator output signals at harmonics of the pulse train frequency, a power amplifier operative to amplify the comb generator output signals so as to produce jamming pulses and an aerial for radiating the jamming pulses, the width of the pulses of the pulse train being short enough to ensure that the harmonics of the pulse train frequency occur throughout the bandwidth.

8 Claims, 3 Drawing Figures

JAMMER TRANSMITTER

This invention relates to transmitters and more especially it relates to R.F. (radio frequency) jammers.

R.F. jammers seek to provide an R.F. signal which interferes with radio communication to an extent which renders the reception of intelligence difficult if not impossible.

The power required to jam a radio communication link depends principally on the range of the radio receiver to be jammed and the bandwidth used by the radio receiver to be jammed. Thus a local receiver using a narrow bandwidth may be jammed with a comparatively small radiated jamming signal whereas a distant communication link occupying a wide bandwidth would require a comparatively large radiated jamming signal if jamming were to be effective.

The foregoing observations will be quite apparent to those skilled in the art and it will also be apparent that the transmission of large amplitude wide bandwidth jamming signals, within the range of communication links which must remain unaffected, would be highly undesirable. It follows therefore that radiated jamming power should be sufficient only to achieve the object, and consequently jaming should be limited to the precise frequency of significance and the jamming transmitter should be operated as close as possible to the receiver to be jammed.

In order to make effective jamming difficult, various anti-jamming techniques are employed and perhaps the most effective of these techniques is the technique of frequency hopping. Frequency hopping requires a radio frequency to be changed or hopped periodically so that a transmission is in effect distributed over a wide bandwidth although occupying instantaneously a comparatively narrow bandwidth only. It is not easy to design a jammer which will hop synchronously with the signal to be jammed, and saturation jamming over a wide band has inherent serious disadvantages. Frequency hopping transmissions are therefore not easy to jam effectively and hitherto an effective cheap and simple jammer has not been available. It is an object of the present invention to provide such a jammer.

According to the present invention a jammer transmitter comprises a comb spectrum generator which includes pulse generator means adapted to produce a pulse train at a frequency corresponding to the channel spacing of signals to be jammed, and a bandpass filter which has a passband including or controllable to include, a bandwidth occupied by the signals to be jammed and which is responsive to the pulse train for providing within this bandwidth comb generator output signals at harmonics of the pulse train frequency, a power amplifier operative to amplify the comb generator output signals so as to produce jamming pulses and aerial means for radiating the jamming pulses, the width of the pulses of the pulse train being short enough to ensure that the harmonics of the pulse train frequency occur throughout the said bandwidth.

The pulse generator means may comprise an oscillator arranged to provide a signal at the channel spacing frequency and a monostable device responsive to the oscillator for producing the said pulse train.

The monostable device may be a monostable multivibrator or alternatively it may comprise a step recovery diode.

The monostable device may be arranged to feed the bandpass filter via an amplifier.

The bandpass filter may be controllable to afford various passbands which may be adjacent and contiguous thereby to cover a predetermined frequency band in steps.

The jammer may be contained within a case including a battery compartment.

The case may be adapted to fit into an aerial transportation vehicle.

This vehicle may be an unpowered shell, glider, or projectile, or alternatively it may be powered by means of a rocket engine or some other engine arranged to drive an air screw.

The vehicle may be equipped with a deployable parachute for landing purposes.

One embodiment of the present invention will now be described solely by way of example with reference to the accompanying drawings in which:

FIG. 2 is a waveform diagram showing waveforms generated by the jammer shown in FIG. 1 and in which;

Figure 1:
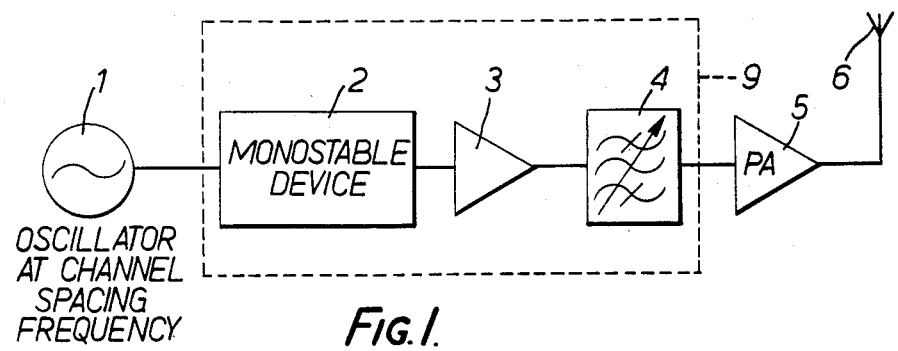
FIG. 1 is a generally schematic block diagram of a jammer.

Referring now to FIG. 1, the jammer comprises an oscillator 1 which is arranged to produce a signal at 25 kHz which corresponds to the channel spacing of signals to be jammed. The oscillator 1 is arranged to feed a monostable device 2, which may be a monostable multivibrator or a step recovery diode for example, which serves to convert the signal from the oscillator into a corresponding train of 30 nanosecond pulses and thus the frequency of the pulse train corresponds to the frequency of the oscillator 1 i.e. 25 kHz. Output signals from the monostable device 2 are fed to an amplifier 3, and the amplifier 3 is arranged to feed a controllable bandpass filter 4. In the present example, the passband of the filter 4 is 30 to 90 mHz and since the pulse width of the pulses is only 30 nanoseconds, harmonics of the pulse train frequency of 25 kHz will extend throughout the 30 to 90 mHz band. It will be appreciated by those skilled in the art that the shorter the pulses produced by the monostable device 2, the further out into the high frequency spectrum will the harmonics potentially extend. And conversely harmonics from longer pulses will not extend so far into the frequency spectrum. Thus if for example one microsecond pulses were generated, the harmonics would probably not extend much beyond 10 mHz, whereas if pulses shorter than 30 nanoseconds were used, a band higher than 90 mHz would be covered.

The signal produced at the output of the filter 4 thus comprises jamming signals spaced apart by the channel spacing frequency i.e. 25 kHz which extend throughout the 30 to 90 mHz band and which therefore may be described as a comb spectrum. The monostable device 2, the amplifier 3 and the filter 4, which are enclosed by a broken line may thus be described as a comb spectrum generator 9.

The jamming pulse train produced by the comb spectrum generator 9 is fed to a power amplifier 5 which is arranged to feed a transmission aerial 6.

Figure 2:
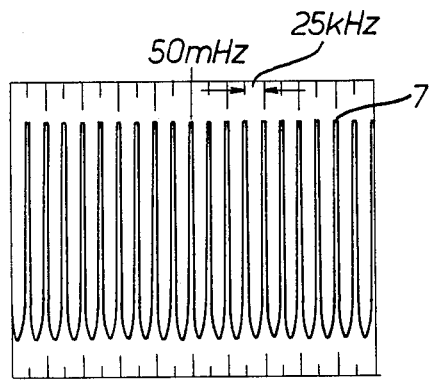

The comb spectrum radiated from the aerial 6 is shown in FIG. 2 and comprises a plurality of signals 7 which extend throughout the 30 to 90 mhz band and which are spaced apart by 25 kHz.

Various modifications may be made to the arrangement shown in FIG. 1 without departing from the scope of the invention and for example the bandpass filter 4 may be switchable to cover a wide bandwidth in steps.

It is desirable that the jammer should not use power unnecessarily and accordingly a more complex jammer will now be described with reference to FIG. 3 which utilizes the basic elements of the jammer described with reference to FIG. 1 but which is arranged to radiate jamming signals only when a signal to be jammed is present.

Figure 3:
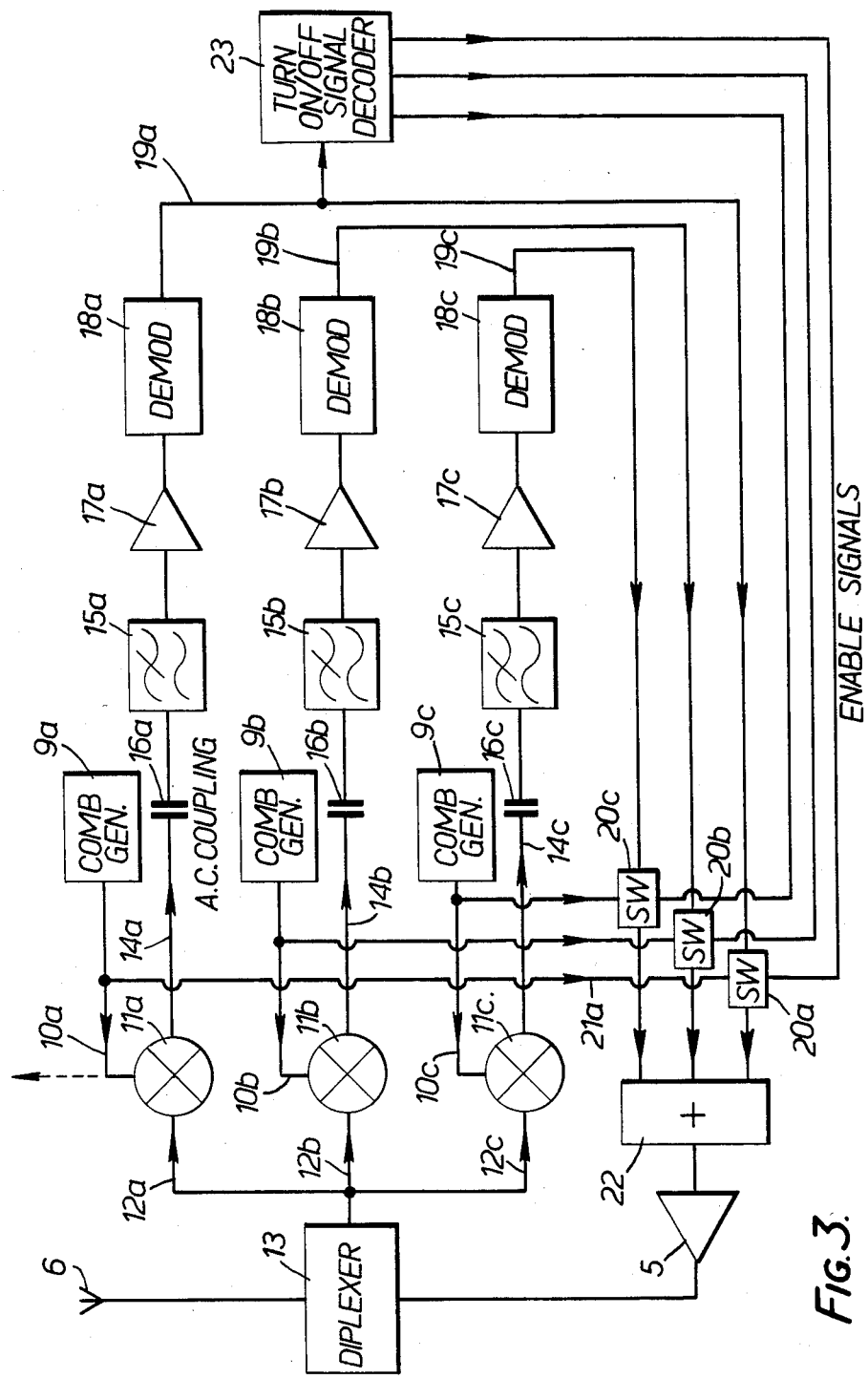
FIG. 3 is a somewhat schematic block diagram of a more complex jammer incorporating the jammer of FIG. 1.

Referring now to FIG. 3 the jammer comprises three comb spectrum generators 9a, 9b and 9c which cover in combination a frequency band to be jammed. Thus in the present case the comb spectrum generator 9a covers the 30 to 50 MHz band, the comb spectrum generator 9b covers the 50 to 70 MHz band, and the comb spectrum generator 9c covers the 70 to 90 MHz band.

The jammer of FIG. 3 includes both the power amplifier 5 and the aerial 6 shown in FIG. 1, but as will hereinafter be described, one or other or all of the comb spectrum generators 9a, 9b and 9c may be arranged to feed the aerial 6 via the power amplifiers. The arrangement and operation of apparatus operatively associated with the comb spectrum generators 9a, 9b and 9c is similar and therefore the operation of the apparatus associated with the comb generator 9a only will be described in detail.

Signals from the comb generator 9a are fed via a line 10a to a mixer 11a to which received signals are fed via a line 12a from the aerial 6 via a diplexer 13. When the frequency of received line 12a falls within the bandwidth covered by the comb spectrum generator 9a low frequency resultant signals will be produced on a line 14a at the output of the mixer 11a which is arranged to feed a low pass filter 15a via a capacitor 16a. The pass band of the filter 15a is arranged to be such that signals are passed by the filter only when the frequency of received signals on the line 12a is such as to correspond with or nearly correspond with the frequency of a signal produced by the comb generator 9a. Output signals from the filter 15a are fed via an amplifier 17a to a demodulator 18a. Signals from the demodulator are fed via a line 19a to a switch 20a. In the presence of a signal on the line 19a, the switch 20a is operated so that signals from the comb spectrum generator 9a produced on a line 21a are fed via the switch 20a to a combiner 22, output signals from which are fed to the amplifier 5. Amplified signals produced by the comb spectrum generator 9a are fed via the diaplexer 13 to the aerial 6 to be radiated as a jamming signal.

It will therefore be appreciated that signals from the comb spectrum generator 9a are fed to the power amplifier 5 only when a signal is received via the aerial 6 which falls within the frequency spectrum covered by the comb spectrum generator 9a.

As hereinbefore explained the comb spectrum generators 9a, 9b and 9c each cover separate adjacent frequency bands and have operatively associated with them similar apparatus corresponding parts of which bear the same numerical designations, the various parts being distinguished by the suffixes a, b, or c, in accordance with the comb spectrum generator with which they are operatively associated. Thus the lines 12a, 12b, and 12c are arranged to feed the mixers 11a 11b and 11c respectively which are operatively associated with the comb generators 9a, 9b and 9c respectively. Therefore if a signal in the frequency band 30 to 50 MHz is received signals from the comb spectrum generator 9a will be fed via the switch 20a and the combiner 22 to the amplifier 5 and similarly if a signal in the frequency band 30 to 70 MHz is received the switch 20b will be operated and signals from the comb spectrum generator 9b will be fed via the combiner 22 and the amplifier 5 through the diplexer 13 to the aerial 6 for jamming purposes. Thus signals will be radiated throughout the whole of the 30 to 90 MHz band if the whole band is used by a frequency hopping transmitter or transmitters and in this case all three of the comb spectrum generators 9a, 9b, and 9c will be used. Alternatively any two or any one of the comb spectrum generators may be used in accordance with the frequency of signals received.

The arrangement shown in FIG. 3 has the advantage that locally generated signals are not fed back to operate the switches 20a, 20b and 20c. This is because signals fed back from the amplifier 5 via the diplexer 13 to the mixers 11a, 11b and 11c are coherent with the signals fed to the mixers 11a, 11b and 11c on the lines 10a, 10b and 10c, and thus the resultant signals prouced on the lines 14a, 14b and 14c at the output of the mixers will be d.c. signals which will blocked by the capacitors 16a, 16b and 16c.

It might normally be arranged however that the diplexer 13 is a signal splitter which affords a higher impedance path to signals fed from the amplifiers 5 to the mixers 12a, 12b and 12c than to signals fed from the amplifier 5 to the aerial 6, whereby saturation of the mixers is avoided.

In order to control the jammer shown in FIG. 3 remotely, a decoder 23 is included which is responsive to predetermined coded signals which in the present example are transmitted in the 30 to 50 MHz band so as to appear on the line 19a at the output of the demodulator 18a. Signals from the decoder 23 are arranged to operate one or other or all of the switches 20a, 20b, or 20c to turn the switches 'ON' or 'OFF', in dependance upon the coded signals transmitted and received on the line 19a. Thus a jammer may be delivered to a remote location and controlled remotely by means of transmitted coded signals.

It will be appreciated that a jammer as just before described with reference to FIG. 3 has the advantage that the power amplifier 5 is utilized for jamming purposes only when predetermined signals to be jammed are received. Apart from effecting a significant power economy, this feature renders the jammer difficult to detect since the jammer operates only in the presence of a signal to be jammed and this will tend to confuse direction finding equipment.

Various modifications may be made to the arrangement described with reference to FIG. 3 and for example the decoder 23 may be arranged to control operation of the power amplifier directly. Although not shown in the drawing, a threshold gate or gates may be included whereby the jammer will operate only in the presence of received signals above a predetermined amplitude and the demodulation 18a, 18b and 18c may for example be arranged to feed the switches 20a, 20b and 20c via threshold gates.

By providing a jammer according to the present invention, jamming power is peaked throughout the frequency band of significance at intervals corresponding to the channel spacing of the signals to be jammed. It will be appreciated therefore that a radio receiver hopping at frequencies within a predetermined band covered by the jammer will find no channel which is free from interference. It will also be appreciated that since a jammer according to the invention concentrates the available power into slots which are spaced apart at intervals throughout the band, high power as would be required for saturation jamming to cover the same frequency band, is not required. It will also be appreciated that a jammer according to the present invention can be made which is small, cheap and robust. Thus jammers according to the present invention may be expendable and delivered in a projectile to a precise location in the proximity of a receiver to be jammed.

I claim:

1. A jammer transmitter comprising a comb spectrum generator which includes pulse generator means adapted to produce a pulse train at a frequency corresponding to the channel spacing of signals to be jammed, and a bandpass filter which has a passband including a bandwidth occupied by the signals to be jammed and which is responsive to the pulse train for providing within this bandwidth comb generator output signals at harmonics of the pulse train frequency, said transmitter further comprising a power amplifier operative to amplify the comb generator output signals so as to produce jamming pulses and aerial means for radiating the jamming pulses, the width of the pulses of the pulse train being short enough to ensure that the harmonics of the pulse train frequency occur throughout the said bandwidth.

2. A transmitter as claimed in claim 3 including a signal decoder responsive to the reception of predetermined coded signals for operating the switch means thereby to afford the provision of a remote control function.

3. A transmitter as claimed in claim 1 comprising switch means via which signals from the comb spectrum generator are fed to the aerial means, mixer means fed from the comb spectrum generator and from the aerial means with received radio signals, and demodulator means responsive to output signals from the mixer means produced in response to the reception of radio signals which fall within the bandwidth covered by the comb spectrum generator, for providing a switch operating signal in the presence of which signals are fed via the switch means from the comb spectrum generator to the aerial means.

4. A transmitter as claimed in claim 3 wherein the switch means is connected between the comb spectrum generator and the power amplifier.

5. A transmitter as claimed in claim 3, wherein the mixer is arranged to feed the demodulator means via low pass filter means and ac coupling means.

6. A transmitter as claimed in claim 3, comprising a plurality of mixers each fed from a comb spectrum generator and fed also with received signals from the aerial means, the frequency of the signals produced by the comb spectrum generators being such that each mixer covers a discrete frequency bandwidth, a plurality of demodulators one for each mixer and a plurality of switch means one fed from each demodulator, each demodulator being operative to provide for the switch means with which it is associated, a switch operating signal responsively to the reception of radio signals by the mixer from which it is fed, which fall within the bandwidth of the comb spectrum generator with which it is operatively associated, whereby signals from that comb spectrum generator are fed via the switch means and the power amplifier to the aerial means.

7. A transmitter as claimed in claim 6 wherein each switch means of the said plurality of switch means is arranged to feed the power amplifier via a signal combiner.

8. A transmitter as claimed in claim 3 including diplexer means via which received signals are fed to the mixer means from the aerial means and via which signals are fed from the power amplifier to the aerial means.

* * * * *